(12) United States Patent
Saunamaki et al.

(10) Patent No.: US 10,743,787 B2
(45) Date of Patent: Aug. 18, 2020

(54) NOISE MITIGATION FOR BIOSIGNALS

(71) Applicant: INTEL CORPORATION, Santa Clara, CA (US)

(72) Inventors: Esa Saunamaki, Virrat (FI); Markus Osa, Pirkanmaa (FI)

(73) Assignee: INTEL CORPORATION, Santa Clara, CA (US)

( * ) Notice: Subject to any disclaimer, the term of this patent is extended or adjusted under 35 U.S.C. 154(b) by 809 days.

(21) Appl. No.: 15/393,932

(22) Filed: Dec. 29, 2016

(65) Prior Publication Data

US 2018/0184932 A1 Jul. 5, 2018

(51) Int. Cl.
*A61B 5/04* (2006.01)
*G16H 10/60* (2018.01)
*G16H 40/40* (2018.01)
*G16H 40/63* (2018.01)
(Continued)

(52) U.S. Cl.
CPC ...... *A61B 5/04017* (2013.01); *A61B 5/04004* (2013.01); *A61B 5/0428* (2013.01); *A61B 5/7203* (2013.01); *G16H 10/60* (2018.01); *G16H 40/40* (2018.01); *G16H 40/63* (2018.01)

(58) Field of Classification Search
CPC ........ G16H 10/60; G16H 40/40; G16H 40/63; A61B 5/04017; A61B 5/04004; A61B 5/0428; A61B 5/7203
See application file for complete search history.

(56) References Cited

U.S. PATENT DOCUMENTS

2006/0098531 A1\* 5/2006 Gardner ................ E21B 47/16 367/82
2008/0294019 A1\* 11/2008 Tran ..................... A61B 5/0006 600/301
2012/0323132 A1 12/2012 Warner et al.
(Continued)

FOREIGN PATENT DOCUMENTS

WO 2009059194 A1 5/2009
WO WO 2009/059194 \* 5/2009

OTHER PUBLICATIONS

Repovs G, "Dealing with Noise in EEG Recording and Data Analysis", Informatica Medica Slovenica (2010).\*
(Continued)

*Primary Examiner* — Catherine T. Rastovski
(74) *Attorney, Agent, or Firm* — Finch & Maloney PLLC

(57) ABSTRACT

A noise detection sensor structure provides hardware-assisted real-time artifact detection on a live bio signal of interest while that signal is being recorded. The structure is configured to detect and analyze the type of external noise, and to use information about the noise type (such as noise level, frequency range of noise, noise source) to improve signal quality and usability of the bio signal. Different algorithms can be used for each noise type detected. In some example cases, for instance, the structure is configured to at least one of extract noise from measurement signal, synchronize measurement with noise signal, change the software filter or analysis algorithm, change gain/filter settings of noise mitigation circuitry, and prompt user to assist as needed, based on the detected noise. Bad signal epochs can be discarded prior to recording, to efficiently use storage. Separate channel(s)/sensor(s) can be used, with different filtering/gain schemes, for noise detection.

25 Claims, 7 Drawing Sheets

(51) Int. Cl.
*A61B 5/00* (2006.01)
*A61B 5/0428* (2006.01)

(56) References Cited

U.S. PATENT DOCUMENTS

| | | |
|---|---|---|
| 2013/0057660 A1 | 3/2013 | Kim et al. |
| 2015/0073234 A1 | 3/2015 | Inan et al. |
| 2015/0126818 A1 | 5/2015 | Fung et al. |
| 2016/0045183 A1 | 2/2016 | Lee et al. |

OTHER PUBLICATIONS

International Search Report and Written Opinion received for PCT/US2017/063432, dated Feb. 8, 2018. 15 pages.

International Preliminary Report and Written Opinion received for PCT/US2017/063432. dated Jul. 2, 2019, pages.

Kaniusas, E., "Biomedical Signals and Sensors I, Linking Physiological Phenomena and Biosignals,". Springer, 2012. XVIII. . 21 pages.

Almeida, M., Bioglasses: Biosignal-based Biometrics using Sensors, Instituto Superior Tecnico, Lisboa, Portugal. Dec. 2014. pp. 1-10.

* cited by examiner

NOISE MITIGATION FOR BIOSIGNALS

BACKGROUND

Biosignals generally refer to detectable signals generated by a living organism, typically a human. The signals may be, for instance, electrical, magnetic, mechanical, acoustical, chemical, or thermal, in nature. In any such cases, an appropriate sensor is used to detect the bio signal of interest and translate that signal into meaningful information about the body (e.g., brain activity, heart activity, eye activity, to name a few examples). Electrical signals generated by the body are typically sensed using an electrode applied to the body near the origin of the electrical signal, such as on the head to detect brain-based signals or on the chest to detect heart-based signals. The electrical signal captured by the electrode may then be amplified to a signal strength suitable for subsequent processing and analysis (e.g., patient diagnosis based on detected signal). Some example use cases where electrical biosignals are monitored include: electroencephalography (EEG) for monitoring electrical brain activity; electrocardiogram (ECG) for monitoring electrical heart activity; electromyogram (EMG) for monitoring electrical muscle activity; and electrooculography (EOG) for monitoring electrical eye activity. Some sensor technology can detect electric biosignals without contacting the body, such as remote sensors for monitoring heart or brain activity of patients who cannot be touched, such as those with sensitive skin or burns. Other non-electrical body signals can be sensed using a transducer that converts the body signal to an electrical signal, such as an acoustic transducer that converts sounds to an electrical signal, or an electrochemical sensor that converts chemical reaction to an electrical signal. The resulting signal can then be amplified and processed. In any such cases, biosignals detection systems can be susceptible to noise. Traditionally, biosignal detection systems such as EEG, ECG or EOG systems utilize software-based artifact (noise) detection algorithms like independent component analysis (ICA) or signal space projection (SSP) for identifying noise artifacts from recorded data and marking relevant epochs as invalid. Thus, an unwanted noise component of the recorded biosignals can be ignored to provide better accuracy. Unfortunately, there are a number of non-trivial issues associated with such noise detection techniques.

Figure 1:
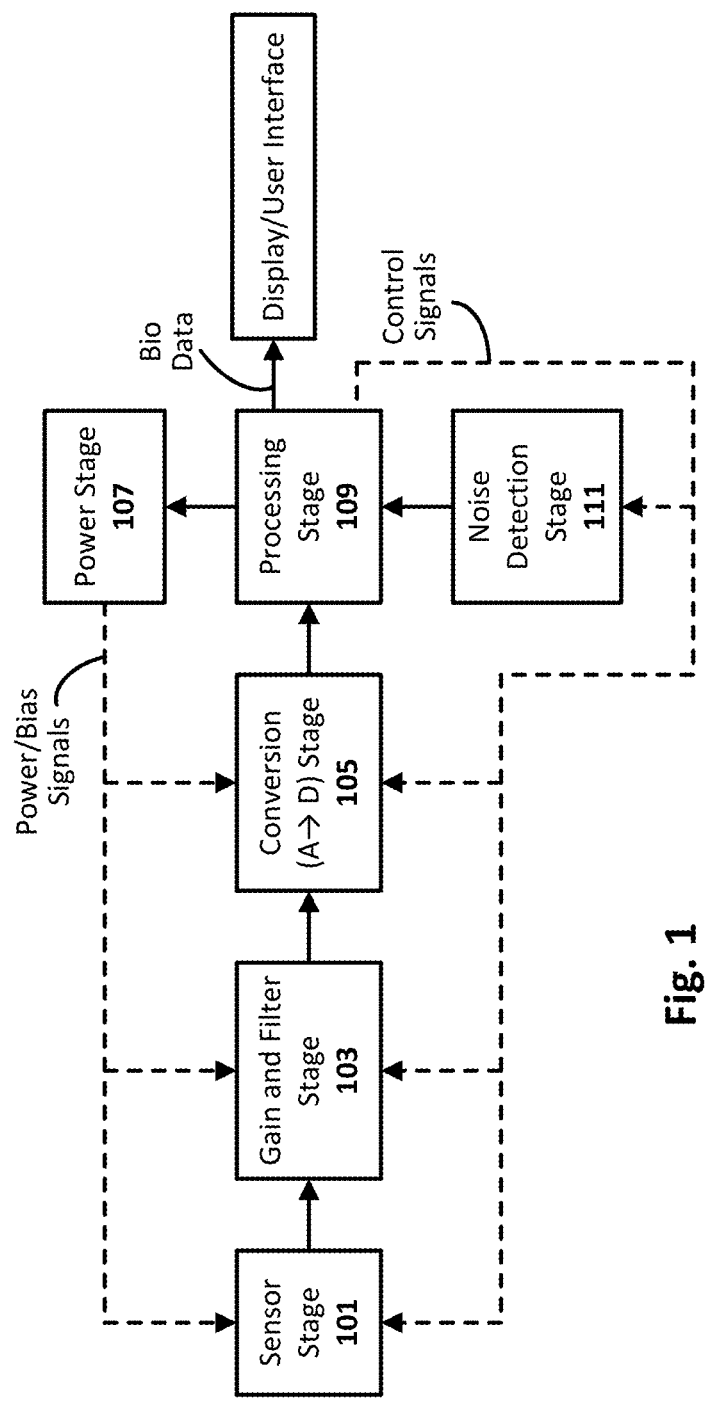
FIG. 1 is a block diagram of bio signal measuring system configured with noise mitigation in accordance with an embodiment of the present disclosure.

These and other features of the present embodiments will be understood better by reading the following detailed description, taken together with the figures herein described. In the drawings, each identical or nearly identical component that is illustrated in various figures may be represented by a like numeral. For purposes of clarity, not every component may be labeled in every drawing.

DETAILED DESCRIPTION

Noise mitigation techniques for biosignals are disclosed. The techniques can be embodied, for instance, in a noise detection sensor structure that provides hardware-assisted real-time artifact detection on a live bio signal of interest while that signal is being recorded. The structure is configured to detect and analyze the type of external noise, and to use information about the noise type (such as noise level, frequency range of noise, and noise source) to improve signal quality and usability of the bio signal of interest. Different filter algorithms can be used for each noise type detected. In some example cases, for instance, the structure is configured to at least one of extract noise from measurement signal, synchronize measurement with noise signal, change the software filter or analysis algorithm, change gain/filter settings of noise mitigation circuitry, and prompt user to assist as needed, based on the detected noise. Bad signal epochs can be discarded prior to recording of signal to efficiently storage. Separate channel(s)/sensor(s) can be used, with different filtering/gain schemes, to address signal diversity (e.g., one or more bio signal channels and one or more noise channels).

General Overview

As previously noted, there are a number of non-trivial issues associated with bio detection systems that utilize software-based artifact detection algorithms like ICA or SSP to identify noise artifacts from recorded signal data and then mark relevant epochs as invalid. An epoch collectively refers to an event marker (onslaught of noise) and a corresponding event window (duration of noise). For instance, software-based algorithms are usually run as a separate post-acquisition processing step on a continuous recorded digitized signal. Such processing on a continuous recorded digitized signal is helpful to avoid filtering effects that may result from using smaller time segments. However, such continuous recording can be a challenge for real-time use cases with strict memory constraints, such as EEG, ECG, EOG, and embedded systems. Moreover, note that each software algorithm is programmed to detect only a particular type of noise artifact. Thus, unexpected external noise signals may be left unmitigated or cause an error state. Further note that traditional bio signal systems rely only on data from the actual bio signal sensors relevant to the application for artifact detection. Thus, external interference may not be registered. For at least one or more of these reasons, existing bio detection systems may not provide enough information for identifying the noise type and for choosing the most appropriate software algorithm for noise detection and rejection.

Thus, noise mitigation techniques for biosignals are disclosed. The techniques can be used to improve noise immunity of biosignal detection systems with respect to external interference such as, ESD, transients, surges, and RF-based interference signals (generally, noise). Any number of biosignal detection contexts can utilize the techniques, including medical, consumer health and safety products, and laboratory contexts, to name a few examples. Specific example applications include heart monitor and brain-computer interface applications, although any number of other applications can equally benefit. In an embodiment, a noise detection sensor structure is employed to detect external interference (e.g., RF interference, ESD interference, power supply switching/charging noise, or other electrical noise) in real-time. The structure is configured to detect and analyze the type of external noise, and to use information about the noise type (such as noise level and frequency range, or the source of the noise, or the modulation type of the noise, or the periodicity information or the noise such as a short pulse or burst of noise at every 100 msec, or some combination of such information) to improve signal quality and usability of the bio signal of interest. In some example cases, for instance, the structure is configured to at least one of extract noise from measurement signal, synchronize measurement with noise signal (to facilitate noise extraction), change the software filter or analysis algorithm, change hardware settings (e.g., change gain factor), and guide user to move the sensor electrode to a noise free position or turn off an electrical device operating in the area or otherwise prompt user to assist in bio monitoring application, based on the detected noise.

The structure thus enables hardware-assisted real-time artifact detection on a live bio signal of interest while that bio signal is being recorded. Different algorithms can be used with different noise types encumbering the same bio signal, thus allowing for complex noise mitigation. Bad signal epochs can be immediately discarded or flagged without requiring the whole signal to be stored in memory, thereby efficiently using available memory. Distinct and separate channel(s)/sensor(s) can be used, potentially with different filtering and gain schemes/saturation points, to address signal diversity (e.g., one or more bio signal channels and one or more noise channels). In some cases, for instance, the noise detection channels/circuitry can be similar to the bio sensor channels/circuitry, but have different gain settings and different passbands. In some such cases, the gain settings and frequency response of each noise channel can be configured in real-time after a particularly noise signal is detected and identified. In some cases, the noise detection structure includes its own receiver and channel dedicated to noise mitigation. Thus, the noise mitigation circuitry can run independently of the bio signal detection system. As such, the bio sensing system can be shutoff or otherwise put on hold until the noise is sufficiently mitigated, thereby preventing recordation of corrupted bio signal data.

As will be further appreciated in light of this disclosure, once the type of noise is identified, one or more appropriate mitigation actions can then be determined and carried out in real-time so as to ensure quality of the recorded bio signal in a given situation. For instance, the mitigation action may include selecting the most appropriate software algorithm for removing the given noise type. Alternatively, or in addition to, the mitigation action may include identifying the noise signature that corresponds to the type, including the noise frequency response and magnitude, and setting a frequency passband and saturation points to isolate and remove the given noise type. Alternatively, or in addition to, the mitigation action may include identifying the noise signature that corresponds to the type, including the noise source, and prompting the user to turn-off the noise source. Alternatively, or in addition to, the mitigation action may include identifying that the noise is being caused by a bad electrode interface, and prompting the user to move the electrode to a different location. Alternatively, or in addition to, the mitigation action may include identifying that the area in which the bio signal sensing is being carried out is too noisy, and prompting the user that bio sensing will be halted until the noise subsides or that the given environment is too noisy for the bio sensing device being used.

System Architecture

FIG. 1 is a block diagram of bio signal measuring system configured with noise mitigation in accordance with an embodiment of the present disclosure. As can be seen, the system includes a sensor stage 101, a gain and filter stage 103, a conversion stage 105, a power stage 107, a processing stage 109, and a noise reduction stage 111. The resulting bio data output of the system can be, for example, presented by a display or user interface. For instance, the bio data may be indicative of electrical heart activity and be presented on an ECG display screen or ticker tape (or other output device). Alternatively, the bio data may be indicative of electrical brain activity and be presented to an EEG display, or an EEG-based brain-computer interface. Alternatively, the bio data may be indicative of electrical muscle activity and be presented to an EMG-based muscle-computer interface. Alternatively, the bio data may be indicative of electrical eye activity and be presented to an EOG-based eye-computer interface. Numerous embodiments and use cases will be apparent in light of this disclosure.

The sensor stage 101 may include any type of bio sensor susceptible to external electrical noise. Example bio sensors include EEG, ECG, EMG, and EOG sensors, to name a few examples. The noise may be, for instance, RF noise such as cellular-based noise, WLAN-based noise (e.g., WiFi, Bluetooth, etc), low frequency noise (such as noise resulting from switched mode power supplies or touch screen displays industry, sometimes referred to as charger noise), transient noise resulting from cycling equipment in the vicinity of the bio sensing area, or any other electrical signal that adversely impacts proper measuring of a target bio signal. In some embodiments, multiple bio sensors may be provided in the sensor stage 101, such as both EEG and ECG sensors. Any number of sensor combinations can be used. The sensor(s) may include electrodes for contacting the skin of the subject being bio-monitored, but remote or non-contact sensors, or implanted sensors may be used as well. Numerous bio sensor configurations that are susceptible to external electrical noise can be used, as will be appreciated.

The gain and filter stage 103 receives the bio signals from the sensor stage 101, amplifies those signals to a suitable level, and filters those signals to eliminate signal outside the frequency range of interest. In some embodiments, gain level(s) and/or frequency passband(s) of stage 103 can be adjusted or otherwise controlled in real-time, as will be explained in turn. In embodiments where multiple sensors are used in sensor stage 101, each sensor can effectively have its own gain and filter stage 103, so as to effectively provide distinct sensor channels. Numerous sensor signal gain and filter schemes can be implemented in stage 103, and the present disclosure is not intended to be limited to any particular configurations.

The conversion stage 105 receives the amplified and filtered bio signals from the gain and filter stage 103, and converts those signals from the analogue domain to the digital domain, using an analogue to digital converter (ADC). In some embodiments, ADC parameters such as sampling frequency, reference voltage, and the number of points for averaging of stage 105 can be adjusted, as will be explained in turn. In channelized embodiments having multiple sensors in sensor stage 101, the amplified/filtered output of each sensor channel can be provided to a multiplexor of stage 105, which in turn switches each bio signal into the ADC. Numerous A→D conversion schemes can be implemented in stage 105, and the present disclosure is not intended to be limited to any particular configurations.

The processing stage 109 receives the digitized bio signals from the conversion stage 105, and further receives noise signal data from the noise detection circuit 111, and may perform any further needed processing and analysis of those signals. Based on the analysis, the processing stage 109 may initiate one or more noise mitigation actions as will be further discussed in turn. This may include, for instance, outputting one or more control signals to any of stages 101, 103, 105, and 111, as generally shown in this example embodiment, to facilitate noise mitigation. Numerous other control schemes will be apparent in light of this disclosure. In addition, a resulting bio data output (with relatively high noise immunity) is output by the processing stage 109. This bio data can be, for example, presented via display or other output device, or used to control a process. So, for example, bio data indicative of electrical activity of the brain or heart of a patient in a healthcare setting may be displayed on corresponding medical gear. Alternatively, bio data indicative of electrical activity of a computer system user's eye or arm or hand muscle may be provided to a user interface of the computer system, and be treated as a user input. Alternatively, bio data indicative of a jogger's heart rate may be provided to a display in conjunction with a prompt telling the use to slowdown or go faster. Numerous such use cases will be appreciated in light of this disclosure.

The noise detection stage 111 may include any type of noise sensor capable of sensing external electrical noise, and provides noise signal data to the processing stage 109. Example noise sensors include, for instance, a wireless receiver such as an RF receiver or a low frequency receiver, an ADC, and an ESD sensor, to name a few examples. As previously explained, the noise may be RF noise such as cellular-based noise, WLAN-based noise, low frequency noise, transient noise resulting from power-cycling electronic equipment in the vicinity of the bio sensing area, or any other electrical noise signal that adversely impacts proper measuring of a target bio signal. In some embodiments, multiple noise sensors may be provided in the noise detection stage 111, such as both an RF sensor (e.g., in the range of 3 KHz to 300 GHz) and a low frequency sensor (e.g., in the range of 50 Hz to 3 KHz). Any number of sensor combinations can be used. The sensor(s) may include, for example, an antenna or electrodes for picking up the noise signals to be mitigated. Numerous noise sensor configurations can be used, depending on the target noise environment, as will be appreciated in light of this disclosure.

The power stage 107 is responsive to the processing stage 109 and provides power and biasing signals to each of stages 101, 103, and 105, in this example embodiment. Other embodiments may be configured differently. For instance, in a similar embodiment, stage 111 may also receive its power and/or biasing signals from processing stage 109, while in other embodiments only stage 103 receives its power and/or biasing signals from processing stage 109, or no stages receive power and/or biasing signals from processing stage 109. As will be appreciated in light of this disclosure, manipulating a stages power and/or bias signals may help with noise mitigation.

Figure 2:
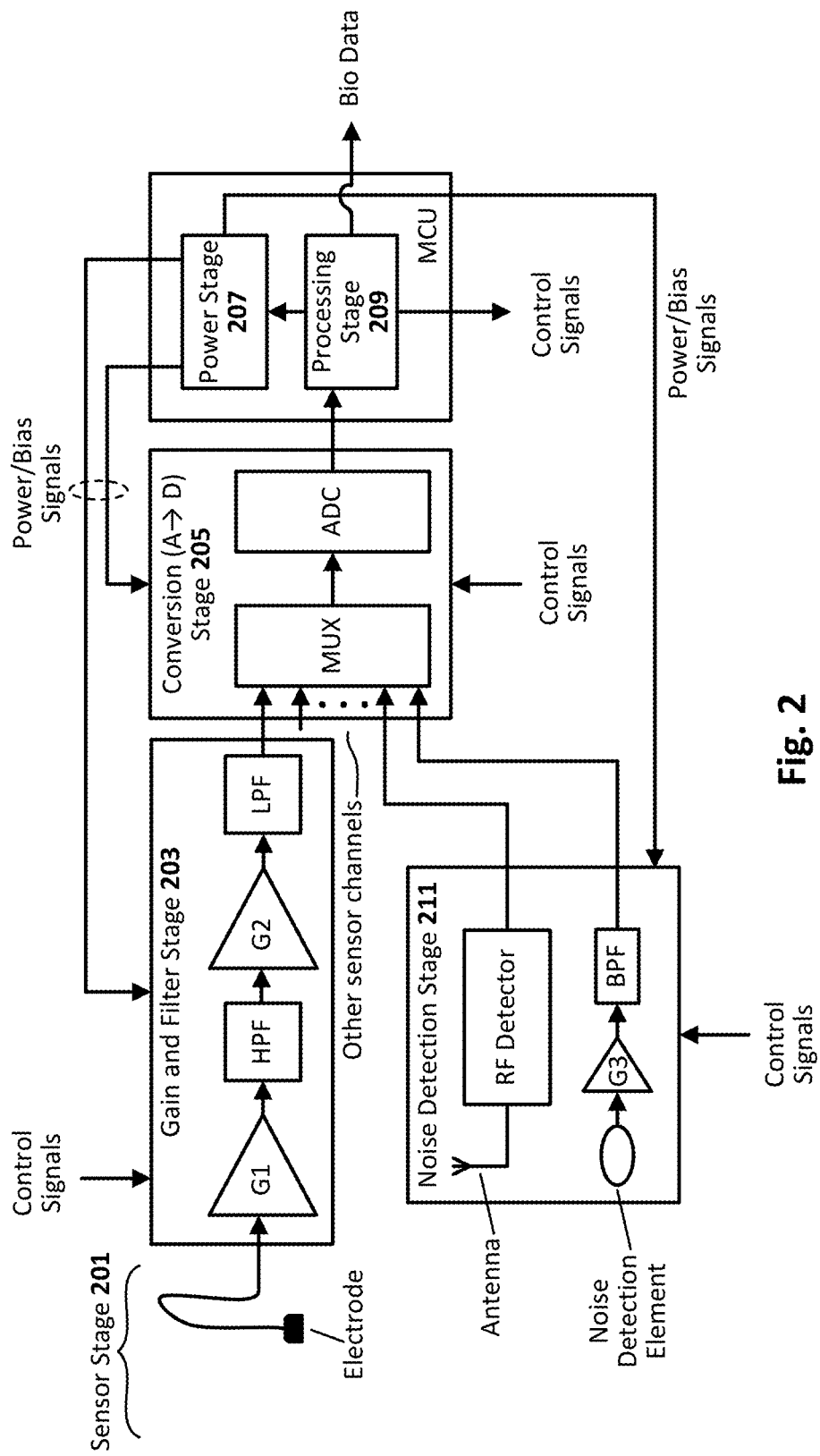
FIG. 2 is a more detailed diagram of bio signal measuring system configured with noise mitigation in accordance with an embodiment of the present disclosure.

FIG. 2 is a more detailed diagram of bio signal measuring system configured with noise mitigation in accordance with an embodiment of the present disclosure. As can be seen, sensor stage 201 includes an electrode which might be placed somewhere on the body, such as the head, chest, arm, or hand. Bio signal captured by the electrode is provided to the gain and filter stage 203, which in this example embodiment includes a first amplifier having a gain of G1, followed by a high-pass filter (HPF), followed by a second amplifier having a gain of G2, followed by a low-pass filter (LPF). The passband of the filter arrangement of course can vary from one embodiment to the next, but in one example case is 0.1 Hz to 100 Hz. In a more general sense, any suitable gain and filter configuration can be used as stage 203. The output of stage 203 is provided the conversion stage 205, which will be discussed in turn. The previous discussion with respect to gain and filter stage 103 is equally applicable here. Although only one bio sensor channel (electrode+stage 203) is shown, note that multiple such channels may be used depending on the desired sensor types and application, as will be appreciated.

The noise stage 211 of this example embodiment includes two types of noise detectors. One is an RF detector (receiver) having an antenna to capture noise signals to be mitigated. The other noise detection element may be, for instance, an ESD sensor, although any electrical noise sensor can be used. The output of this second sensor is provided to an amplifier having a gain of G3, and the amplified output is then filtered through a bandpass filter (BPF). A similar passband to the bio sensor passband can be used (e.g., 0.1 Hz to 100 Hz). Again, numerous configurations can be used here. In any case, the outputs of the noise sensor channels are provided to the conversion stage 205, along with the output of the bio sensor channels. The previous discussion with respect to the conversion stage 105 is equally applicable here. Although two noise sensor channels are shown, note that fewer or more such channels may be used depending on the desired sensor types and application, as will be appreciated. In still other embodiments, note that multiple noise sensors can be connected to and share the same input channel, as long as both noise sensors are not active at the same time (which can be controlled, for example, by the control signals provided by the processing stage 209).

The conversion stage 205 of this example embodiment receives the output of the bio sensor channel(s) from stage 205, and further receives the output of the noise sensor channel(s) from stage 211, and multiplexes those outputs to an ADC. The ADC sequentially converts the analogue signal from each channel to its digital equivalent, and passes the digital signals to a microcontroller unit (MCU) for further processing and analysis. The MCU of this example embodiment generally includes processing stage 209 and power stage 207, and generates a number of signals which in this example embodiment include bio data, power/bias signals, and control signals. The MCU can be configured as desired, and in some cases is configured as a system-on-chip (SoC) or application specific integrated circuit (ASIC) or other purpose-built semiconductor processing architecture. Further details of the MCU will be provided in turn, with reference to the example embodiments depicted in FIGS. 5, 6a, and 6b.

Figure 3:
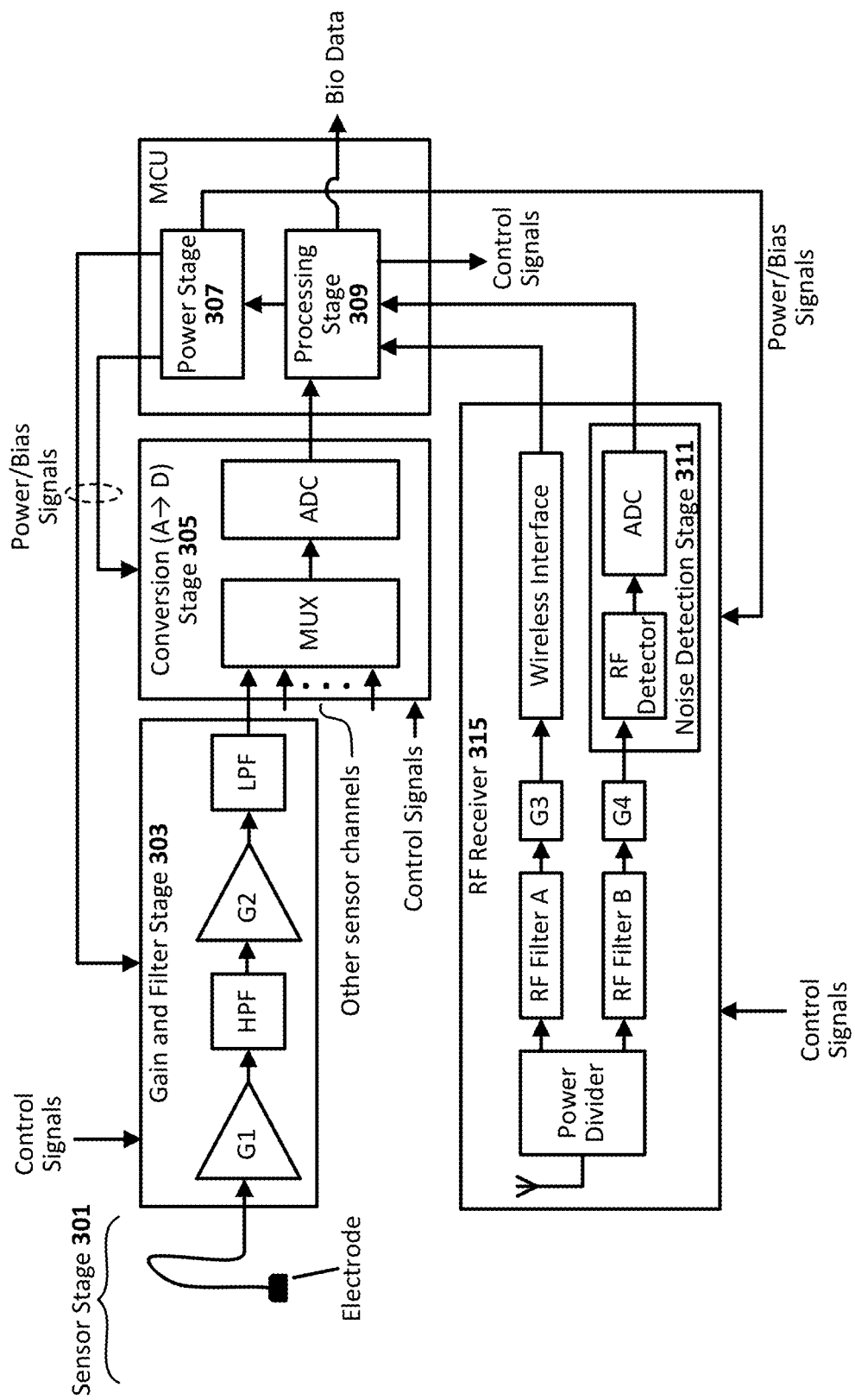
FIG. 3 is a more detailed diagram of bio signal measuring system configured with noise mitigation in accordance with another embodiment of the present disclosure.

FIG. 3 is a more detailed diagram of bio signal measuring system configured with noise mitigation in accordance with another embodiment of the present disclosure. This embodiment is similar to the embodiment shown in FIG. 2, to some extent, and that previous relevant discussion is equally applicable here. However, as can be seen in this example embodiment, the noise detection stage 311 is included in an RF receiver block 315 and includes its own ADC. The RF receiver 315 may be, for example, part of a host computing system, but any number of other configurations will be apparent. In any case, the host system and the noise detection stage 311 use same antenna element. A power divider splits off a first version of the received RF signal which is processed through RF filter A and amplifier G3, and provided as input to the standard wireless interface of the host system. The output of the wireless interface is provided to the processing stage 309. The other output of the power divider provides a second version of the received RF signal which is processed through RF filter B and amplifier G4, and the output is provided to the noise detection stage 311. The noise detection stage 311 includes an RF detector (receiver) and an ADC. Thus, if noise is present in the received RF signal, the bio signal input channels can be shut down (via stages 301 and 305), and noise monitoring can still continue. Note that noise detection stage 311 may further include its own processing stage, so as to remove dependence on the host processing stage 309.

Figure 4:
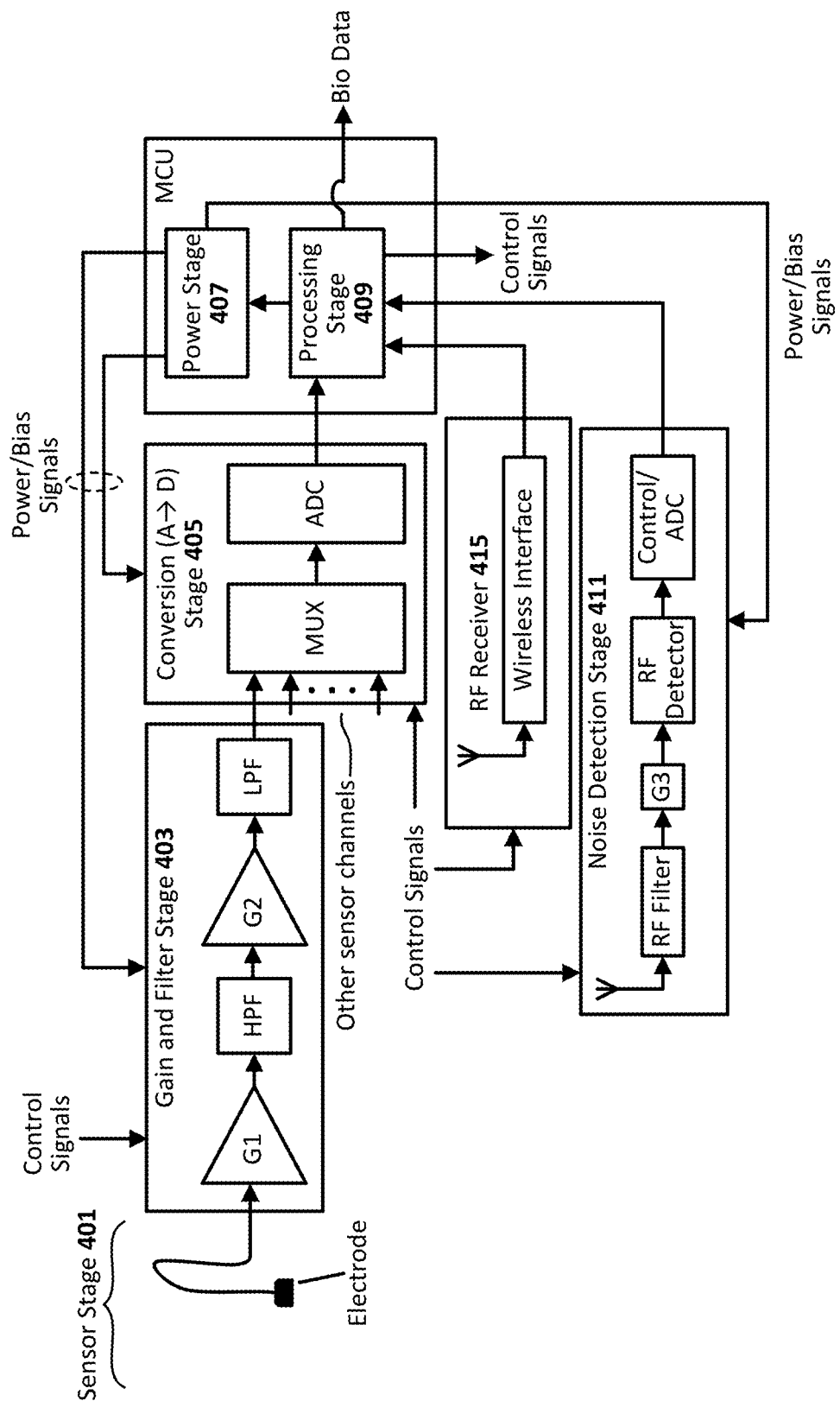
FIG. 4 is a more detailed diagram of bio signal measuring system configured with noise mitigation in accordance with another embodiment of the present disclosure.

FIG. 4 is a more detailed diagram of bio signal measuring system configured with noise mitigation in accordance with another embodiment of the present disclosure. This embodiment is similar to the embodiments shown in FIGS. 2 and 3, to some extent, and that previous relevant discussion is equally applicable here. However, as can be seen in this example embodiment, the noise detection stage 411 includes its own controller and ADC, and is included in a dedicated RF receiver that is in addition to RF receiver block 415. The RF receiver 415 includes an antenna and a standard wireless interface and may be, for example, part of a host computing system, but any number of other configurations will be apparent. The output of the wireless interface is provided to the processing stage 409. In this example embodiment, the noise detection stage 411 uses its own antenna element for noise sensing, and further includes an RF filter, amplifier G3, and RF detector (RF receiver), and a control and ADC block. The antenna can be any type. In some embodiments, the antenna can be part of the mechanical structure of the noise mitigation system. As will be appreciated in light of this disclosure, the noise mitigation system can be tuned for sensing noise in a certain frequency range that is relevant to the noise immunity point performance. Likewise, the RF detector may have more than one channel to detect simultaneously noise from more than one frequency band and/or different types of modulated signals. This kind of independent signal detection also increases safety and reliability in some systems, such as those where cases where user authentication is based on brain or other bio potential signals. Noise detection aspect can also protect system against the unauthorized remote usage. In such a case, someone may try to access to bio sensor system using an RF signal, which is modulated with simulated or recorded brain signal. Note that noise detection stage 411 in this example embodiment includes its own control capability, so as to remove dependence on the host processing stage 409.

Methodology

Figure 5:
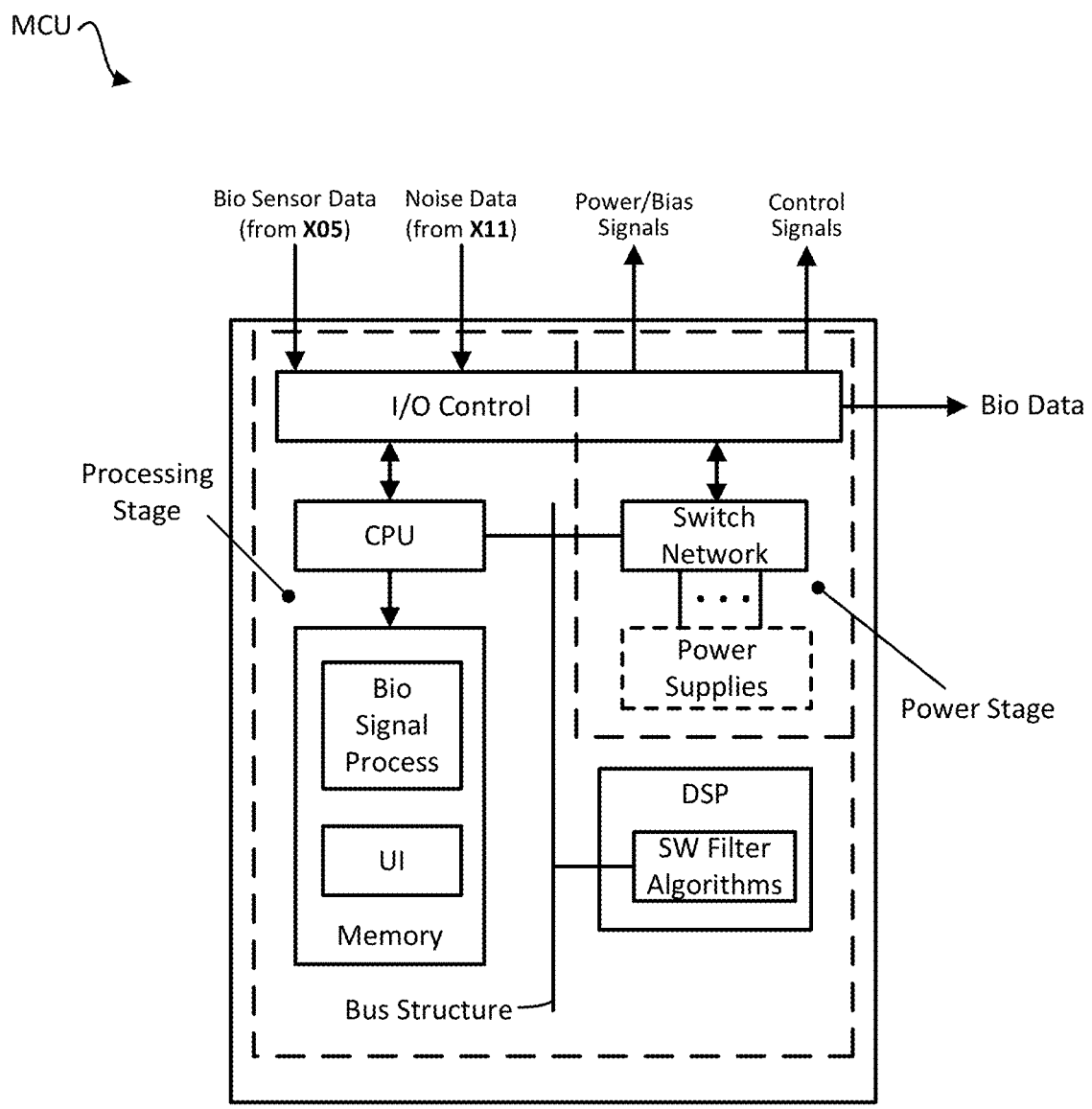
FIG. 5 is a block diagram of a processing environment configured to carry out noise mitigation for a bio sensor system, in accordance with an embodiment of the present disclosure.

FIG. 5 further illustrates an example MCU architecture configured in accordance with an example embodiment of the present disclosure. As can be seen, the processing stage and power stage of the MCU are generally delineated with dashed lines. The processing stage of the MCU of this example configuration includes a CPU, a non-volatile memory, I/O control, and a digital signal processor (DSP). The power stage of the MCU of this example configuration includes a switch network and a set of power supplies, along with I/O control. A bus structure is provided to allow for inter-component communication. An executable bio signal process or routine is stored in the memory, and a number of software filter algorithms are accessible to the DSP. The MCU hardware can be implemented with standard technology, and numerous configurations and variation will be apparent in light of this disclosure. For instance, in some embodiments, note that the power supplies of the power stage may be external to the MCU, as may the switch network. In operation, the I/O control of the MCU receives the bio sensor data and the contemporaneous noise data. The CPU executes the bio signal process stored in the memory to analyze and process that received bio data. In response to that analysis, the CPU then causes a number of signals to be output by the MCU, which in this example embodiment include bio data, power/bias signals, and control signals. These signals may, for example, change gain states, switch in different filter components, change reference voltages, or change saturation points on the relevant stages (201/301/401, 203/303/403, 205/305/405, 207/307/407, 211/311/411, 315/415) to bring about a desired noise mitigation effect.

Figure 6A:
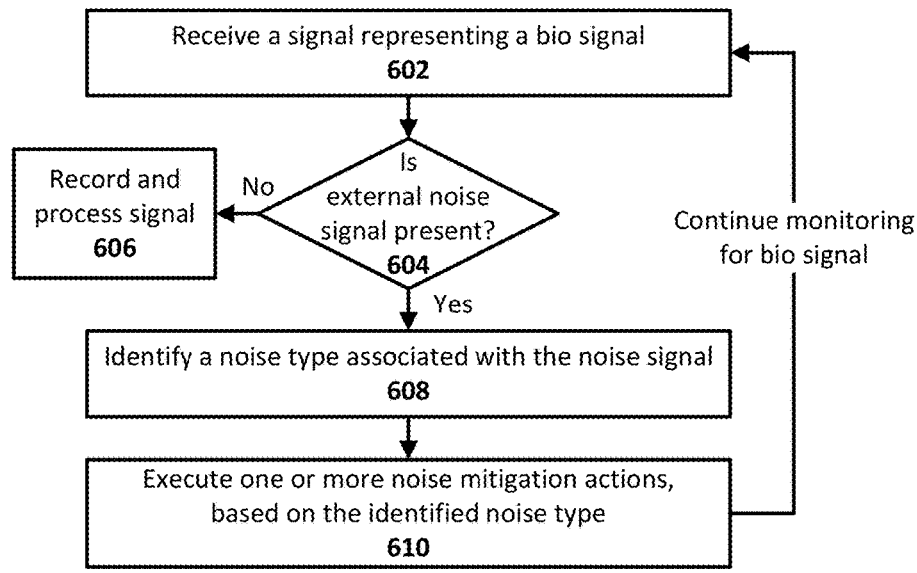
FIGS. 6a and 6b are flowcharts of a methodology for carrying out noise mitigation in a bio signal measuring system, in accordance with an embodiment of the present disclosure.
Figure 6B:
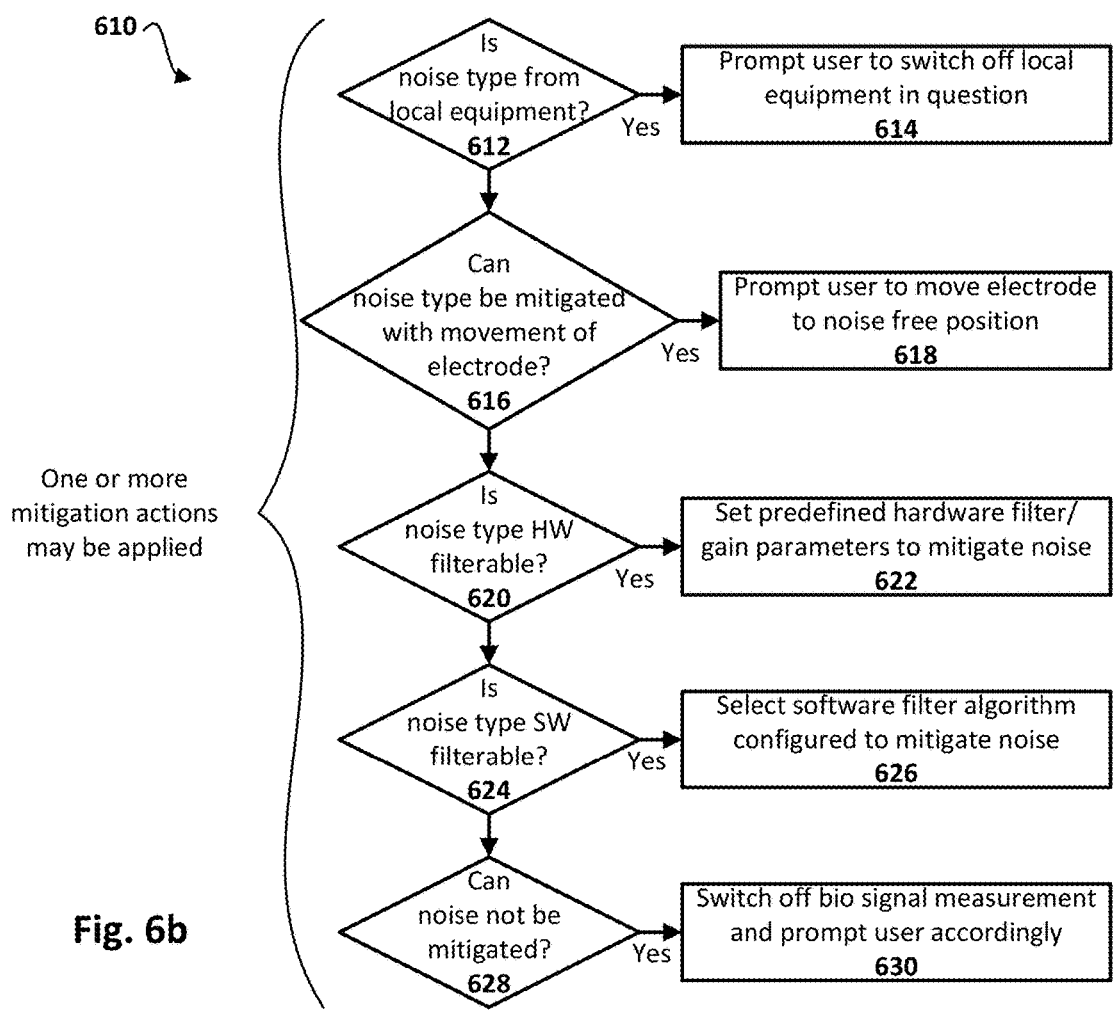

The flowcharts of FIGS. 6a and 6b illustrate the bio signal process executed by the CPU, in accordance with some embodiments of the present disclosure. As can be seen in FIG. 6a, the bio signal process commences with receiving 602 a signal representing a bio signal. Contemporaneously, the process includes a determination at 604 as to whether an external noise signal is present. If not, the process continues with recording 606 and processing the bio signal. On the other hand, if external noise signal is present, the process continues with identifying 608 a noise type associated with the noise signal, and executing 610 one or more noise mitigation actions, based on the identified noise type. The process continues to monitoring for bio signals and repeats until noise is sufficiently mitigated or there are no bio signals to process.

As can be seen in example embodiment of FIG. 6b, any number of noise mitigation actions can be carried out at 610, depending on the circumstances as assessed by the CPU. So, in this example case, the CPU is capable of determining at 612 whether the noise type is from local electronic equipment that may be operating in the vicinity. If so, the mitigation action executed by the CPU may include prompting 614 the user to switch off the local equipment in question. The prompt may be presented to the user by a display or the system, or some other intuitive output mechanism. The process of noise mitigation continues with the CPU determining at 616 whether the noise type can be mitigated with movement of the bio sensor electrode. If so, the mitigation action executed by the CPU may include prompting 618 the user to move the bio sensor electrode to a noise free position on the subject being tested.

The process of noise mitigation continues with the CPU determining at 620 whether the noise type can be mitigated with a hardware filter or component. If so, the mitigation action executed by the CPU may include setting 622 predefined hardware filter/gain parameters to remove or otherwise mitigate noise. Note this can be accomplished, for example, by the CPU outputting control signals to the noise detection stage 211/311/411, to change gain states and/or switch in different filter components. Likewise, the CPU can output power/bias signals to the conversion stage 205/305/405 to improve signal-to-noise ratio (SNR) of system.

The process of noise mitigation continues with the CPU determining at 624 whether the noise type can be mitigated with a software filter. If so, the mitigation action executed by the CPU may include selecting 626 a software filter algorithm to remove or otherwise mitigate noise. Note this can be accomplished, for example, by the CPU directing the DSP which digital filter to use. DSP algorithms or filters reduce signal noise by removing unwanted frequency components of the digitized signal. Example DSP filters include infinite impulse response (IIR) filters, finite impulse response (FIR) filters, convolvers, and Faster Fourier Transforms (FFT). In a more general sense, any suitable software filters can be selected to mitigate noise from the bio sensor system. In some example embodiments, the appropriate digital filters are identified in a look-up table that is indexed by the noise type. Thus, the CPU can readily identify an appropriate digital filter based on the detected noise type.

The process of noise mitigation continues with the CPU determining at 628 whether the noise type cannot be mitigated. If so, the mitigation action executed by the CPU may include switching 630 off the bio signal measurement and prompt user accordingly, or otherwise disable the bio signal collection and/or analysis until the contemporaneous noise ceases or is otherwise mitigated. Note this can be accomplished, for example, by the CPU directing the switch network of the MCU to disconnect the power supplies powering the bio sensor channels, or by CPU outputting control signals to disable the sensor stage 201/301/401 or the gain and filter stage 203/303/403 or the conversion stage 205/305/405. As will be further appreciated, shutting down processing of sensor signals can be used to avoid the situation where a pre-amplifier or other circuitry in the bio sensor system rectifies or otherwise processes a noise signal and generates misleading bio data.

Figure 7A:
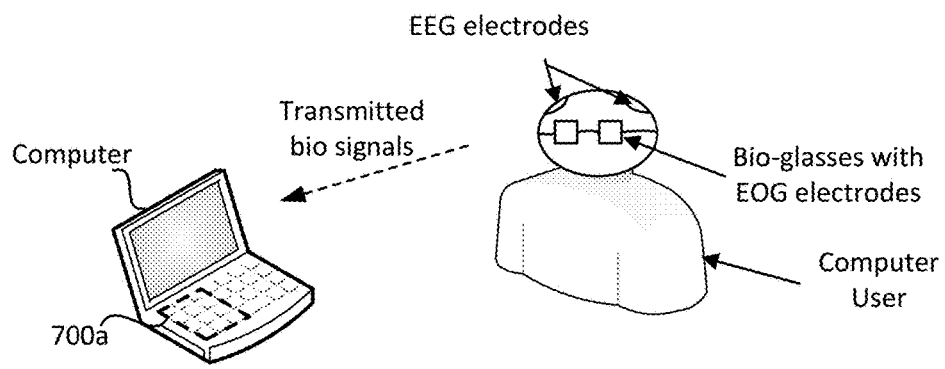
FIGS. 7a through 7c illustrate example use cases for a bio signal measuring system configured with noise mitigation, in accordance with an embodiment of the present disclosure.
Figure 7B:
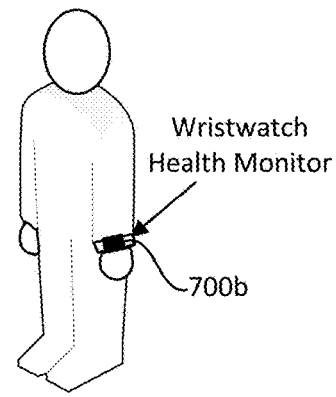
Figure 7C:
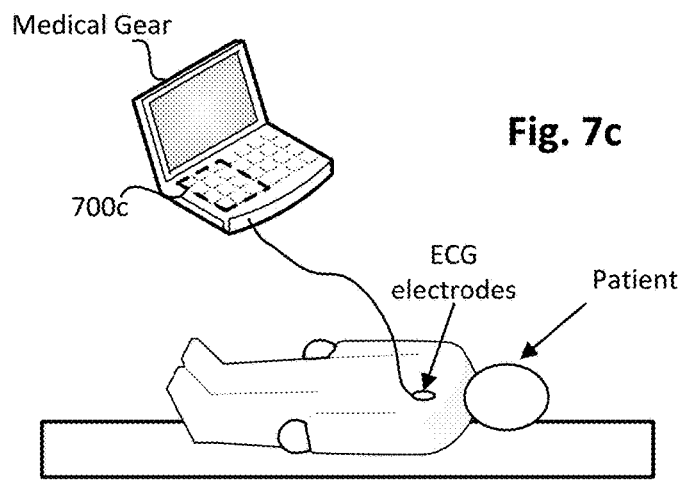

FIGS. 7a through 7c each illustrates an example use case for a bio signal measuring system configured with noise mitigation, in accordance with an embodiment of the present disclosure. As can be seen in FIG. 7a, EEG-based bio data indicative of electrical brain activity of a computer system user, and EOG-based bio data indicative of electrical eye activity of the computer system, are being transmitted to a user interface of the computer system, and treated as a user input by the computer system. The computer system includes a bio sensor system configured with noise mitigation, as generally indicated at 700a. As can be seen in FIG. 7b, bio data indicative of a jogger's heart rate (pulse) is being provided to a wristwatch display in conjunction with a prompt telling the user to slowdown or go faster, as the case may be. The wristwatch includes a bio sensor system configured with noise mitigation, as generally indicated at 700b. As can be seen in FIG. 7c, ECG-based bio data indicative of a patient's electrical heart activity is being provided to medical gear. The medical gear includes a bio sensor system configured with noise mitigation, as generally indicated at 700c. Each of the systems 700a-c can be configured, for example, like any of the example embodiments shown in FIGS. 1-6b. Numerous other embodiments and example uses cases will be appreciated, including embodiments that utilize any combination of the various architectures and form factors depicted or otherwise described with respect to FIGS. 1-7c.

Further Considerations

For embodiments that include independent noise sensors (such as shown in FIGS. 2 and 4), note that the noise detection sensors/antennas can be designed so that they do not detect the bio potential signals. Thus, for example, the noise sensors can be placed so that they are not directly against the body (head, chest, hand, arm, eye area, etc) like the bio sensors may be. Further note that some noise types can be identified by a unique signature or one or more signal qualities that can be detected, such as frequency range and level of the noise. For instance, in some cases, such signal qualities can be based on analysis in electromagnetic compatibility lab. Once qualities of a given noise signal are known, the impact of that noise signal on the noise immunity of a given bio sensing system can also be assessed. So, for example, the impact on the critical frequency ranges of a bio sensor system can be known for a particular noise signal.

As will be further appreciated, note that a noise mitigation system configured in accordance with an embodiment of the present disclosure can be programmed or otherwise configured to detect cellular transmit signals and/or low frequency noise signals over a specified trigger level (e.g., mobile phone based noise, touch screen device based noise, and/or switching power supply based noise). In such example cases, when an external noise signal is detected, the bio sensor system may change its configuration in any number of ways. For instance, the system may change from using a first sensor type to second sensor type, or add in a second sensor type, via a switching arrangement controlled by the processing stage. Likewise, the system may change hardware and/or software algorithm settings to minimize impact on usability of the system (e.g., change reference voltages to improve SNR). Likewise, the system may change the user interface (UI) of the system so as to guide or otherwise prompt the user to change location of the sensor, or to switch off specific devices (e.g., turn off cell phone).

In the case of ESD, a bio sensor system ideally can recover from an ESD event automatically, without user actions (reboot device, etc). Thus, in some embodiments, the noise detection stage can detect and recognize an ESD event, if the ESD level is over a specified trigger level. The system can then use that information, for example, as a basis for initiating an automatic software ESD refresh function, or some other action to mitigate fallout from the ESD event.

FURTHER EXAMPLE EMBODIMENTS

The following examples pertain to further embodiments, from which numerous permutations and configurations will be apparent.

Example 1 is a sensor system, comprising: a bio sensor stage to detect an analog bio signal; a noise sensor stage to detect an analog noise signal that originates external to the system; and a processor stage configured to, in response to determining that an analogue noise signal is present contemporaneously with an analogue bio signal, identify a noise type associated with the analogue noise signal, and execute one or more noise mitigation actions, based on the identified noise type.

Example 2 includes the subject matter of Example 1, and further includes at least one of: an amplifier to amplify a detected analog bio signal; a filter to filter a detected analog bio signal; and a conversion stage to convert a detected analog bio signal to a digital bio signal.

Example 3 includes the subject matter of Example 2, and further includes a power supply stage to provide at least one of power and bias signals to one or more of the bio sensor stage, noise sensor stage, amplifier, filter, and conversion stage, in response to direction from the processor stage.

Example 4 includes the subject matter of Example 2 or 3, wherein the conversion stage includes a multiplexor and an analogue-to-digital converter (ADC), the multiplexor allowing for multiple sensor channels providing input to the ADC.

Example 5 includes the subject matter of Example 4, wherein the bio sensor stage includes one or more bio sensor types, each bio sensor type connected to a different sensor channel.

Example 6 includes the subject matter of Example 4 or 5, wherein the noise sensor stage includes one or more noise sensor types, each noise sensor type connected to a different sensor channel.

Example 7 includes the subject matter of any of the preceding Examples, wherein: the bio sensor stage includes one or more bio sensor types for detecting electrical biosignals, including at least one of an electroencephalography (EEG) sensor for detecting electrical brain activity, an electrocardiogram (ECG) sensor for detecting electrical heart activity, an electromyogram (EMG) sensor for detecting electrical muscle activity, and an electrooculography (EOG) sensor for detecting electrical eye activity; and the noise sensor stage includes one or more noise sensor types for detecting noise signals, including at least one of an RF receiver for detecting noise signals having a frequency of 3 KHz or higher, a low frequency receiver for detecting noise signals having a frequency below 3 KHz, an analogue-to-digital converter (ADC), and an electrostatic discharge (ESD) sensor.

Example 8 includes the subject matter of any of the preceding Examples, and further includes a power supply stage to provide at least one of power and bias signals to one or more of the bio sensor stage and noise sensor stage, in response to direction from the processor stage.

Example 9 includes the subject matter of any of the preceding Examples, wherein the processor stage is further configured to, in response to determining that no analogue noise signal is present contemporaneously with an analogue bio signal, record the bio signal in a memory.

Example 10 includes the subject matter of Example 9, wherein the recorded bio signal is used to control a computing device.

Example 11 includes the subject matter of Example 9 or 10, wherein the recorded bio signal is used to present patient diagnostics.

Example 12 includes the subject matter of Example 9, 10, 11, wherein the recorded bio signal is used to present health diagnostics.

Example 13 includes the subject matter of any of the preceding Examples, wherein the processor stage is further configured to continuously monitor for bio signals until noise is sufficiently mitigated or there are no bio signals to process.

Example 14 includes the subject matter of any of the preceding Examples, wherein executing one or more noise mitigation actions, based on the identified noise type, includes at least one of presenting a prompt to a user to facilitate mitigation of the analogue noise signal, setting predefined hardware filter parameters to facilitate mitigation of the analogue noise signal, setting predefined hardware gain parameters to facilitate mitigation of the analogue noise signal, selecting a software filter algorithm from a plurality such algorithms to facilitate mitigation of the analogue noise signal, and disabling at least one of bio signal collection and analysis.

Example 15 includes the subject matter of any of the preceding Examples, wherein the noise sensor stage is configured to not detect bio signals that the bio sensor stage detects.

Example 16 includes the subject matter of any of the preceding Examples, wherein the noise sensor stage and the bio sensor stage share an antenna, but have separate receivers.

Example 17 includes the subject matter of any of Examples 1 through 15, wherein the noise sensor stage and the bio sensor stage have separate receivers and separate antennas.

Example 18 includes the subject matter of any of the preceding Examples, wherein the noise sensor stage and the bio sensor stage share an analog-to-digital converter (ADC), the ADC for converting analogue noise and bio signals to digital signals.

Example 19 includes the subject matter of any of the preceding Examples, wherein the processor stage includes a central processing unit (CPU), a digital signal processor (DSP), and a memory.

Example 20 includes a sensor system, comprising: a bio sensor stage including one or more types of noise sensors for detecting electrical biosignals, including at least one of an electroencephalography (EEG) sensor for detecting electrical brain activity, an electrocardiogram (ECG) sensor for detecting electrical heart activity, an electromyogram (EMG) sensor for detecting electrical muscle activity, and an electrooculography (EOG) sensor for detecting electrical eye activity; a noise sensor stage to detect an analog noise signal that originates external to the system; and a microcontroller configured to in response to determining that an analogue noise signal is present contemporaneously with an analogue bio signal, identify a noise type associated with the analogue noise signal, and execute one or more noise mitigation actions, based on the identified noise type, and in response to determining that no analogue noise signal is present contemporaneously with an analogue bio signal, record the bio signal in a memory.

Example 21 includes the subject matter of Example 20, wherein executing one or more noise mitigation actions, based on the identified noise type, includes at least one of presenting a prompt to a user to facilitate mitigation of the analogue noise signal, setting predefined hardware filter parameters to facilitate mitigation of the analogue noise signal, setting predefined hardware gain parameters to facilitate mitigation of the analogue noise signal, selecting a software filter algorithm from a plurality such algorithms to facilitate mitigation of the analogue noise signal, and disabling at least one of bio signal collection and analysis.

Example 22 includes the subject matter of Example 20 or 21, wherein the noise sensor stage is configured to not detect bio signals that the bio sensor stage detects.

Example 23 is computer program product including one or more non-transitory process readable mediums encoded with instructions that when executed by one or more processors cause a process to be carried out for noise mitigation in a bio sensor system, the process comprising: receiving a signal representing an analog bio signal; in response to determining that an analogue noise signal is present contemporaneously with an analogue bio signal, identifying a noise type associated with the analogue noise signal, and executing one or more noise mitigation actions, based on the identified noise type, wherein the analog noise signal originates external to the bio sensor system; and in response to determining that no analogue noise signal is present contemporaneously with an analogue bio signal, recording the bio signal in a memory.

Example 24 includes the subject matter of Example 23, wherein: the signal representing an analog bio signal is one of an electroencephalography (EEG) sensor signal indicative of electrical brain activity, an electrocardiogram (ECG) sensor signal indicative of electrical heart activity, an electromyogram (EMG) sensor signal indicative of electrical muscle activity, and an electrooculography (EOG) sensor signal indicative of electrical eye activity; and the analogue noise signal is one of an RF noise signal having a frequency of 3 KHz or higher, a low frequency noise signal having a frequency below 3 KHz, an electrostatic discharge (ESD) signal, a switchable power supply noise signal, a cellular phone noise signal, or a touch screen display noise signal.

Example 25 includes the subject matter of Example 23 or 24, wherein the recorded bio signal is used to at least one of control a computing device, present patient diagnostics, and present health diagnostics.

Example 26 includes the subject matter of any of Examples 23 through 25, the process further including continuously monitoring for bio signals until noise is sufficiently mitigated or there are no bio signals to process.

Example 27 includes the subject matter of any of Examples 23 through 26, wherein executing one or more noise mitigation actions, based on the identified noise type, includes presenting a prompt to a user to facilitate mitigation of the analogue noise signal.

Example 28 includes the subject matter of any of Examples 23 through 27, wherein executing one or more noise mitigation actions, based on the identified noise type, includes setting predefined hardware filter parameters to facilitate mitigation of the analogue noise signal.

Example 29 includes the subject matter of any of Examples 23 through 28, wherein executing one or more noise mitigation actions, based on the identified noise type, includes selecting a software filter algorithm from a plurality such algorithms to facilitate mitigation of the analogue noise signal.

Example 30 includes the subject matter of any of Examples 23 through 29, wherein executing one or more noise mitigation actions, based on the identified noise type, includes disabling at least one of bio signal collection and analysis carried out by the bio sensor system.

The foregoing description of example embodiments has been presented for the purposes of illustration and description. It is not intended to be exhaustive or to limit this disclosure to the precise forms disclosed. Many modifications and variations are possible in light of this disclosure. It is intended that the scope of this disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

What is claimed is:

1. A sensor system, comprising:
    a bio sensor stage configured to detect an analog bio signal;
    a noise sensor stage configured to detect an analog noise signal that originates external to the sensor system; and
    a processor stage configured to, in response to determining that the analog noise signal is present contemporaneously with the analog bio signal,
        detect a noise signal type associated with the analog noise signal,
        select one or more noise mitigation actions from a plurality of possible noise mitigation actions that can be used to mitigate the analog noise signal, wherein the selection is based at least in part on the detected noise signal type, and
        execute the one or more noise mitigation actions.

2. The system of claim 1, further comprising at least one of:
    an amplifier to amplify a detected analog bio signal;
    a filter to filter a detected analog bio signal; and
    a conversion stage to convert a detected analog bio signal to a digital bio signal.

3. The system of claim 2, further comprising:
    a power supply stage to provide at least one of power and bias signals to one or more of the bio sensor stage, noise sensor stage, amplifier, filter, and conversion stage, in response to direction from the processor stage.

4. The system of claim 2, wherein the conversion stage includes a multiplexor and an analog-to-digital converter (ADC), the multiplexor allowing for multiple sensor channels providing input to the ADC.

5. The system of claim 4, wherein the bio sensor stage includes one or more bio sensor types, each bio sensor type connected to a different sensor channel.

6. The system of claim 4, wherein the noise sensor stage includes one or more noise sensor types, each noise sensor type connected to a different sensor channel.

7. The system of claim 1, wherein:
    the bio sensor stage includes one or more bio sensor types for detecting electrical biosignals, including at least one of an electroencephalography (EEG) sensor for detecting electrical brain activity, an electrocardiogram (ECG) sensor for detecting electrical heart activity, an electromyogram (EMG) sensor for detecting electrical muscle activity, and an electrooculography (EOG) sensor for detecting electrical eye activity; and
    the noise sensor stage includes one or more noise sensor types for detecting noise signals, including at least one of an RF receiver for detecting noise signals having a frequency of 3 KHz or higher, a low frequency receiver for detecting noise signals having a frequency below 3 KHz, an analog-to-digital converter (ADC), and an electrostatic discharge (ESD) sensor.

8. The system of claim 1, further comprising:
    a power supply stage to provide at least one of power and bias signals to one or more of the bio sensor stage and noise sensor stage, in response to direction from the processor stage.

9. The system of claim 1, wherein the processor stage is further configured to, in response to determining that no analog noise signal is present contemporaneously with an analog bio signal, record the bio signal in a memory.

10. The system of claim 9, wherein the recorded bio signal is used to control a computing device.

11. The system of claim 9, wherein the recorded bio signal is used to present patient diagnostics.

12. The system of claim 9, wherein the recorded bio signal is used to present health diagnostics.

13. The system of claim 1, wherein the processor stage is further configured to continuously monitor for bio signals until noise is sufficiently mitigated or there are no bio signals to process.

14. The system of claim 1, wherein executing the one or more noise mitigation actions includes at least one of presenting a prompt to a user to facilitate mitigation of the analog noise signal, setting predefined hardware filter parameters to facilitate mitigation of the analog noise signal, setting predefined hardware gain parameters to facilitate mitigation of the analog noise signal, selecting a software filter algorithm from a plurality of software filter algorithms to facilitate mitigation of the analog noise signal, and disabling at least one of bio signal collection and analysis of any detected bio signals.

15. The system of claim 1, wherein the noise sensor stage is configured to not detect bio signals that the bio sensor stage detects.

16. The system of claim 1, wherein the noise sensor stage and the bio sensor stage share an antenna, but have separate receivers.

17. The system of claim 1, wherein the noise sensor stage and the bio sensor stage have separate receivers and separate antennas.

18. The system of claim 1, wherein the noise sensor stage and the bio sensor stage share an analog-to-digital converter (ADC), the ADC for converting analogue noise and bio signals to digital signals.

19. The system of claim 1, wherein the processor stage includes a central processing unit (CPU), a digital signal processor (DSP), and a memory.

20. A sensor system, comprising:
a bio sensor stage including one or more types of sensors configured for detecting electrical biosignals, including at least one of an electroencephalography (EEG) sensor for detecting electrical brain activity, an electrocardiogram (ECG) sensor for detecting electrical heart activity, an electromyogram (EMG) sensor for detecting electrical muscle activity, and an electrooculography (EOG) sensor for detecting electrical eye activity;
a noise sensor stage configured to detect an analog noise signal that originates external to the system; and
a microcontroller configured to
in response to determining that the analog noise signal is present contemporaneously with the analog bio signal, detect a noise signal type associated with the analog noise signal, select one or more noise mitigation actions from a plurality of possible noise mitigation actions that can be used to mitigate the analog noise signal, wherein the selection is based at least in part on the detected noise signal type, and execute the one or more noise mitigation actions, and
in response to determining that no analog noise signal is present contemporaneously with an analog bio signal, record the analog bio signal in a memory.

21. The system of claim 20, wherein executing the one or more noise mitigation actions, includes at least one of presenting a prompt to a user to facilitate mitigation of the analog noise signal, setting predefined hardware filter parameters to facilitate mitigation of the analog noise signal, setting predefined hardware gain parameters to facilitate mitigation of the analog noise signal, selecting a software filter algorithm from a plurality of software filter algorithms to facilitate mitigation of the analog noise signal, and disabling at least one of bio signal collection and analysis of any detected bio signals.

22. The system of claim 20, wherein the noise sensor stage is configured to not detect bio signals that the bio sensor stage detects.

23. A computer program product including one or more non-transitory machine-readable mediums encoded with instructions that when executed by one or more processors cause a process to be carried out for noise mitigation in a bio sensor system, the process comprising:
receiving a signal representing an analog bio signal;
in response to determining that an analog noise signal is present contemporaneously with the analog bio signal, detecting a noise signal type associated with the analog noise signal, selecting one or more noise mitigation actions from a plurality of possible noise mitigation actions that can be used to mitigate the analog noise signal; wherein the selection is based at least in part on the detected noise signal type, and executing the one or more noise mitigation actions, wherein the analog noise signal originates external to the bio sensor system; and
in response to determining that no analog noise signal is present contemporaneously with the analog bio signal, recording the analog bio signal in a memory.

24. The computer program product of claim 23, wherein the recorded bio signal is used to at least one of control a computing device, present patient diagnostics, and present health diagnostics.

25. The computer program product of claim 23, wherein executing the one or more noise mitigation actions, includes at least one of: presenting a prompt to a user to facilitate mitigation of the analog noise signal; setting predefined hardware filter parameters to facilitate mitigation of the analog noise signal; selecting a software filter algorithm from a plurality of software filter algorithms to facilitate mitigation of the analog noise signal; and disabling at least one of bio signal collection and analysis carried out by the bio sensor system.

\* \* \* \* \*